United States Patent
Minto et al.

(10) Patent No.: US 9,453,821 B2
(45) Date of Patent: Sep. 27, 2016

(54) MONITORING OF CONDUITS

(75) Inventors: Christopher Minto, Farnborough (GB); Alastair Godfrey, Farnborough (GB)

(73) Assignee: OPTASENSE HOLDINGS LIMITED (GB)

(*) Notice: Subject to any disclaimer, the term of this patent is extended or adjusted under 35 U.S.C. 154(b) by 205 days.

(21) Appl. No.: 14/125,697

(22) PCT Filed: Jun. 20, 2012

(86) PCT No.: PCT/GB2012/051417
§ 371 (c)(1),
(2), (4) Date: Dec. 12, 2013

(87) PCT Pub. No.: WO2012/175954
PCT Pub. Date: Dec. 27, 2012

(65) Prior Publication Data
US 2014/0123759 A1 May 8, 2014

(30) Foreign Application Priority Data
Jun. 20, 2011 (GB) .................................. 1110403.1

(51) Int. Cl.
| | |
|---|---|
| *G01N 29/11* | (2006.01) |
| *F17D 5/00* | (2006.01) |
| *G01H 9/00* | (2006.01) |
| *G01M 3/00* | (2006.01) |
| *G01M 3/24* | (2006.01) |
| *G01M 3/38* | (2006.01) |
| *G01M 5/00* | (2006.01) |
| *G01M 11/08* | (2006.01) |
| *G01V 1/22* | (2006.01) |

(52) U.S. Cl.
CPC ............... *G01N 29/11* (2013.01); *F17D 5/005* (2013.01); *G01H 9/004* (2013.01); *G01M 3/005* (2013.01);
(Continued)

(58) Field of Classification Search
CPC .... G01N 29/11; G01M 3/007; G01M 3/246; G01M 3/38; G01M 3/005; G01M 5/0033; G01M 5/0025; G01M 11/085; F17D 5/005; G01V 1/226

USPC ........................................ 73/643, 655, 657
See application file for complete search history.

(56) References Cited

U.S. PATENT DOCUMENTS 3,561,256 A 2/1971 Bustin et al.
4,927,232 A * 5/1990 Griffiths ................. G01B 11/18
250/227.24

(Continued)

FOREIGN PATENT DOCUMENTS

CN 10132472 9/2010
GB 1120336 7/1968

(Continued)

*Primary Examiner* — Daniel S Larkin
*Assistant Examiner* — Rose M Miller
(74) *Attorney, Agent, or Firm* — McDonnell Boehnen Hulbert & Berghoff LLP

(57) ABSTRACT

This application relates to methods and apparatus for monitoring of conduits, especially oil or gas pipelines, as an object such as pipeline pig moves within the conduit. The method comprises monitoring at least part of a conduit (206) using a fibre optic (202) distributed acoustic sensor (204) as the object (208) passes along the conduit. The acoustic signals detected from at least one sensing location (203) as the object moves along the conduit are analysed so as to discriminate acoustic signals received at said sensing location from different locations. The method allows the contributions to the acoustic signal at a given sensing portion from different locations to be separately identified, and can allow the detection of the location of acoustic sources along the conduit even if the source is outside the section of conduit which is monitored. The method provides a method of leak detection that can extend the monitoring of the pipeline beyond the location of the optical fibre.

21 Claims, 3 Drawing Sheets

(52) U.S. Cl.
CPC ............. *G01M 3/007* (2013.01); *G01M 3/246* (2013.01); *G01M 3/38* (2013.01); *G01M 5/0025* (2013.01); *G01M 5/0033* (2013.01); *G01M 5/0091* (2013.01); *G01M 11/085* (2013.01); *G01V 1/226* (2013.01)

(56) References Cited

U.S. PATENT DOCUMENTS

| | | | |
|---|---|---|---|
| 8,973,444 B2* | 3/2015 | Hill | F17D 5/06 73/623 |
| 2009/0132183 A1* | 5/2009 | Hartog | G01D 5/35303 702/42 |
| 2010/0268489 A1 | 10/2010 | Lie et al. | |
| 2011/0007996 A1* | 1/2011 | Huffman | G01M 5/0025 385/13 |
| 2011/0093220 A1 | 4/2011 | Yang et al. | |
| 2011/0139538 A1 | 6/2011 | Hill et al. | |
| 2011/0149688 A1* | 6/2011 | Hill | F17D 5/06 367/87 |

FOREIGN PATENT DOCUMENTS

| | | |
|---|---|---|
| GB | 2442745 | 4/2008 |
| WO | WO 2010/010318 | 1/2010 |
| WO | WO 2010/020796 | 2/2010 |
| WO | WO 2010/094809 | 8/2010 |

* cited by examiner

MONITORING OF CONDUITS

FIELD OF THE INVENTION

The present invention relates to monitoring conduits, especially oil and gas pipelines, and in particular to using the movement of objects in conduits to improve monitoring and discrimination.

BACKGROUND OF THE INVENTION

Pipelines are the most economically viable method of transporting fluid assets, most commonly oil and gas, but other types of pipeline also exist. A vast pipeline infrastructure exists today responsible for gathering, transporting and distributing these natural resources, with over three quarters of a million kilometers of oil and gas pipelines in the US alone. The continuing proper operation of these pipelines is of paramount importance, and failures carry massive economic loss, environmental impact and potentially catastrophic physical damage also.

Significant efforts are therefore made to maintain, monitor and inspect pipelines. The sheer size of many pipeline networks however, and the fact that many kilometres of pipelines consist of underground or sub-sea installations makes effective and efficient monitoring a difficult problem.

It has been proposed to use fibre optic distributed acoustic sensing to monitor pipelines. International Patent Application Publication WO2010/020796 describes that tens of kilometres of pipeline can be monitored by deploying an optical fibre along the length of the pipeline and interrogating the optical fibre with radiation to provide a fibre optic distributed acoustic sensor. This application teaches that by monitoring the acoustic response of the pipeline to an acoustic stimulus a condition profile of the pipeline can be obtained. The stimulus may be a stimulus deliberately introduced for the purposes of obtaining a condition profile or it could be produced during normal operation of the pipeline, for example as a result of a "pig" travelling through the pipeline.

Various inspection and maintenance tools may be inserted into the pipeline and carried through the pipeline by the pressure of the fluid therein. There are a variety of different objects, commonly referred to as "pigs" that may be employed. A simple cleaning pig may comprise an object shaped to brush or scrape the inner walls of the pipeline as it passes to provide a cleaning action. An intelligent monitoring pig may comprise various sensors to perform various monitoring tasks and an onboard processor and can be a very expensive, very complex instrument.

Use of a pig for inspection or cleaning is commonly referred to as pigging. Pigging is often carried out with largely uninterrupted fluid flow through the pipeline and thus is advantageous in that pipeline flow need not be stopped to perform routine inspection and maintenance.

WO2010/020796 describes that a sudden leak or crack in the pipeline may result in a detectable pressure pulse and that detection of the occurrence of such a spontaneous pulse may be used as part of leak detection and location.

The use of fibre optic distributed acoustic sensing for pipeline monitoring such as taught in WO2010/020796 therefore provides a very useful and convenient way of monitoring large sections of pipeline. The present invention relates to further improvements in relation to monitoring of conduits.

SUMMARY OF THE INVENTION

Thus according to the present invention there is provided a method of conduit monitoring comprising: monitoring at least part of a conduit using a fibre optic distributed acoustic sensor as an object passes along the conduit; and analysing the acoustic signals detected at at least one sensing location as the object moves along the conduit so as to discriminate acoustic signals received at said sensing location from different locations.

The conduit may be a pipeline, for instance an oil or gas pipeline. The object may be a pipeline pig, for example a cleaning or inspection pig.

Embodiments of the present invention rely on the fact that acoustic signals may be transmitted along the conduit, for instance within the fluid within the conduit which may be pressurised. Thus an acoustic source at one location along a pipeline may generate an acoustic signal that is incident on the pipeline. This acoustic signal travel along the pipeline, for instance within the pressurised fluid, for a relatively long distance (and further than the signal would be transmitted through the ground). This may result in an acoustic signal being detected along a significant length of the pipeline. In normal pipeline operation the acoustic signals detected at any location along the pipeline may therefore comprise acoustic signals received from the environment at that location of the pipeline but also some acoustic signals which are due to acoustic sources from a remote location along the pipeline and which have been transmitted along the pipeline.

If such a remote acoustic source is reasonably constant then it may not be able to determine the exact location of the acoustic source from a simple analysis of the acoustic signals. It is known to determine the location of an acoustic source by considering the time of time of arrival of a distinct acoustic signal at different parts of the sensing fibre. However if the acoustic source has a reasonably constant output then it can be difficult to identity arrival of a distinct signal at different part of the sensing fibre.

If the acoustic source is located in a part of the pipeline which is monitored by the distributed fibre optic sensor then it may be possible to determine the location of the acoustic source from the relative intensity of the acoustic disturbance but this may not always be possible. Further if there are several different acoustic sources at different locations the resulting intensity pattern will depend on the location and relatively intensity of the various acoustic sources as well the attenuation that occurs at different parts of the pipeline. Also the acoustic source could be located in a section of pipeline which is not monitored by the distributed acoustic sensor and hence intensity information may not be available as there is no relevant sensing portion of fibre at the source.

The present inventors have realised however that the acoustic signals detected as a pig moves through the pipeline can be analysed to discriminate between acoustic signals received from different locations. When the pig moves between the acoustic source along the pipeline and the relevant sensing portion it will act to increase the attenuation of acoustic signals. In effect the pig will substantially block the acoustic signals from travelling further along the pipeline, or at least significant reduce the intensity of any such signal. Thus consider a sensing portion of the distributed acoustic sensor at a first position along the pipeline and an acoustic source at a second position, downstream (in terms of pipeline flow and thus pig travel) of the first position. In normal operation the acoustic signals from the acoustic source may travel from the second location along the pipeline to the first location and thus may be detected, e.g. as noise, at the first location. In other words the acoustic signals generated by the source are incident on the pipeline at the second location and travel along the pipeline to the first location. When a pig is introduced upstream of the first location it will have no effect on the acoustic signals originating from the source at the second location. As the pig travels down the pipeline it may generate pressure waves as discussed in WO2010/020796, but, as described in this document, such pressure pulses will tend to occur at intervals and have a specific characteristic and so can easily be detected and characterised. After a while the pig will reach and pass the first position. At this point the pig is located in the pipeline between the sensing portion (at the first position) and the acoustic source (at the second location). The presence of the pig will act to significantly attenuate or block the acoustic signals from the source at the second location from reaching the first location. Thus the acoustic signal detected by the sensing portion at the first location will suddenly lose the acoustic contribution from the acoustic source at the second location. Not until the pig has passed the second location, and thus the acoustic source at the second location and sensing portion at the first location are again on the same side of the pig, will the acoustic signal from the source at the second location be again detected at the first location.

The presence of the pig in the pipeline therefore effectively divides the pipeline into two separate sections, upstream and downstream of the pig, and attenuates or blocks signals from the upstream section from propagating to the downstream section and vice versa. Thus a sensing portion located upstream of the pig will generally only receive acoustic signals from other parts of the pipeline upstream of the pig and likewise any downstream sensing portion will generally only receive acoustic signals from downstream sections of the pipeline.

As the pig moves the relevant sections of the pipeline which are upstream and downstream of the pig are effectively scanned along the pipeline thus allowing discrimination of acoustic sources from different sections of the pipeline. For example the method may comprise locating the position along the pipeline of an acoustic source.

As described above if a signal from an acoustic source is received at a first sensing location until the pig has passed that location, at which point the signal is no longer received, then it can be determined that the relevant acoustic source is downstream of the sensing location. The signal will be detected again however as soon as the pig passes the location of the acoustic source. The location of the pig at this point thus indicates the location of the source. If the acoustic source was upstream of the sensing portion however the reverse would happen, the signal would disappear (i.e. cease to be detected at a given sensing portion) as the pig passed the location of the source and would only reappear (i.e. be detected again) once the pig had passed the sensing portion. Thus by analysing the acoustic signals to determine at what point a particular acoustic signal is detected or not detected the position of the relevant acoustic source may be determined through a knowledge of the location of the pig at that time. The method may therefore comprise identifying a first acoustic signal and identifying when the first acoustic signal starts to be detected and/or ceases to be detected. The method may comprise identifying when the first signal both ceases to be detected and re-starts to be detected.

The first signal may be a relatively constant or repetitive signal, i.e. a non-transitory signal. It will be appreciated that a DAS sensor may detect transient signals caused by various events in the location being monitored. Such transient acoustic events will lead to a signal that is detected and then ceases to be detected. The method of the present invention is not concerned with transitory signals but with signals, which in the absence of movement of the object in the pipeline, are relatively continuous or repetitive.

Identifying when a pre-existing signal ceases to be detected may therefore be used to indicate that the pig has moved between the location of the sensing portion and the pig. As mentioned previously for acoustic sources which are upstream of the sensing location the location of the pig at that point thus gives the location of the acoustic source (along the pipeline). Likewise for downstream sources the point at which a signal starts to be detected (or re-detected) indicates that pig has moved beyond the location of the source and thus the location of the pig at that point indicates the location of the source. The method may therefore comprise determining the location of the object at the point that a particular acoustic signal is detected or not detected.

In some instance the location of the pig may be known by tracking devices on the pig or within the pipeline but in some embodiments the location of the pig can be determined from the acoustic signals created by the pig as it moves down the pipeline in the part of the pipeline monitored by the distributed acoustic sensor.

International patent publication WO2010/020795 describes how distributed acoustic sensing may be used to track the motion of a pig in a pipeline.

The method may also comprise analysing the returns from more than on sensing portion of fibre. A signal transmitted along the pipeline may be detected by several distinct sensing portions of fibre and may have a similar characteristic in each sensing portion. The detection/loss of detection of a signal in different sensing portions may also be used to identify the location of a source. For example consider three contiguous sensing portion. All of the three sensing portions may receive acoustic signals which are transmitted along the pipeline from a downstream or upstream source. If the source is upstream of all three sensing portions then as a pig passes the location of the source the signals will cease to be detected in the three sensing portions at substantially the same time (allowing for propagation speed of the acoustic signals in the pipeline). The signals will then be detected again in the three sensing portions in turn as the pig passes each sensing portion. Conversely were the source downstream of the sensing portions then the relevant signals would cease to be detected from each sensing portion in turn as the pig passed the sensing portions, but then would be detected again in all three portions substantially simultaneously when the pig later passes the source. Comparing the responses for several sensing sections may help to identify particular acoustic signals due to a particular acoustic source.

It should be noted that the present invention allows location of an acoustic source along a pipeline to be determined even if the acoustic source is not in the section of pipeline which is monitored by the distributed acoustic sensor. Whatever the location of pig at the point that the relevant acoustic signals cease or resume is the location of the relevant source (potentially adjusting for the time taken for the acoustic signals to travel to the sensing portion). The method of the present invention therefore generally provides a method of extending the sensing capability of a distributed acoustic sensor deployed along as section of a conduit, e.g. to locations upstream and/or downstream of the deployed optical fibre.

The method may enable a method of leak detection in pipelines. Whilst WO2010/020796 describes that a sudden leak or crack may lead to a detectable pressure pulse the location clearly could only be determined if the location of the leak was within the part of the pipeline monitored by the distributed acoustic sensor and the pressure pulse was sufficiently intense. For leaks occurring outside of the monitored part of the pipeline even if there was a relatively intense pressure pulse to point of origin could not be determined. Also some leaks may lead to a general increase in noise level, i.e. a persistent hiss type noise, and may not lead to a pressure pulse. The method of the present invention can allow detection of the location of the sources of persistent noise and hence can offer a method of identifying the location of leaks in a pipeline.

Differential analysis may be applied to the acoustic signals acquired at different pig locations in order to better characterise the noise signals and the location of acoustic sources. Thus the method may comprise applying differential analysis to acoustic signals from a given sensing location acquired with the object at one location and acoustic signals acquired from said sensing location acquired with the object at at least one other location and/or without the object in the conduit. For example a baseline signal acquired with no pig in the pipeline may be compared to a signals acquired with the pig slightly upstream of the relevant sensing location and further to signals acquired with the pig slightly downstream of the relevant sensing location to compare signals from all acoustic source with signals just from downstream sources and signals just from upstream sources. The person skilled in the art of signal processing will be aware of some of the processing techniques that can be applied to such signals to determine useful information about the distribution and intensity of the acoustic sources.

The method thus allows the various contributions to an acoustic signal at a given sensing to be discriminated by detecting when certain contributions are blocked as a pig passes. This also allows any signals which are not at all affected by the passing of the pig to be characterised as originating directly from the rest of the environment at that point (i.e. not being signals that are transmitted along the pipeline).

The discussion above has focussed on a single pig travelling through a pipeline. In some pipelines it may be possible to have more than one pig within the pipeline at a time. For example consider two pigs inserted into a pipeline within a separation of about 300 m. This would effectively divide the pipeline into three sections, upstream of both pigs, downstream of both pigs and the section between the pigs. Whilst this would not provide any increased discrimination for acoustic sources outside the part of the pipeline monitored by the distributed acoustic sensor it may allow additional discrimination within the part of the pipeline monitored by the distributed acoustic sensor.

Embodiments of the invention have been described in terms of movement of a pig in a pipeline but it will be appreciated that the idea applies generally to conduits and to movement of any object in a conduit that is of substantially the same shape/diameter of the conduit, i.e. would act to block or significantly attenuate acoustic signals from propagating past the object in the conduit.

Whilst the data processing may be done in real time as the acoustic signals are being acquired it will of course be appreciated that the data may be acquired during a pigging run and then subsequent analysed. The method in general therefore relates to taking data acquired from at least part of a conduit using a fibre optic distributed acoustic sensor as an object passed along the conduit; and analysing the acoustic signals detected at at least one sensing location as the object moved along the conduit so as to discriminate acoustic signals received at said sensing location from different locations.

Existing optic fibres running along the path of a conduit can be employed for sensing purposes, by connecting suitable interrogation and processing apparatus. For example, a significant proportion of pipelines will have pre-existing lengths of optic fibre running along the path of the pipeline. These are typically communications cables and/or for SCADA (Supervisory Control and Data Acquisition) of the pipeline which were laid at the same time as the pipeline for obvious logistical reasons. In such cases, because existing cables can be made to form part of the monitoring apparatus, relatively long spans of pipeline can be monitored with only limited access to the pipe required.

The sensing fibre for distributed sensing may be located inside the conduit, on the exterior surface of the conduit, directly buried adjacent to the conduit or in a separate adjacent conduit, in various different embodiments. The same fibre may be located at least partly within and at least partly without the conduit. There is no prescribed position for the sensing fibre, provided its location is such that it is able to detect a sufficient response to a pressure pulse within the conduit. Because of the high sensitivities possible in fibre optic sensing, whereby induced phase differences can be measured using interferometric techniques, the potential scope for positioning the fibre, or the scope for selecting an existing fibre is large. Generally speaking however, it is preferable for the fibre to be located at or within approximately 3 m of the fluid carrying conduit, and more preferably at or within approximately 1.5 m from the centreline of the conduit to be monitored.

The spatial resolution of the distributed fibre optic sensing is less than or equal to 30 m in many embodiments, and less than or equal to 20 m or 10 m in certain embodiments. In certain embodiments the optic fibre is interrogated to provide sensed data over a distance greater than or equal to 20 km, and distances of greater than or equal to 30 km or 40 km are achievable in other embodiments.

As mentioned above the method also relates a method of extending the range or sensing capability of a conduit monitoring sensor comprising a fibre optic distributed acoustic sensor having a fibre optic cable deployed along a first section of the conduit, the method comprising analysing the acoustic signals at at least one sensing portion of interest as an object travels through a second section of the conduit (the second section being different to the first section).

The invention also relates to a computer programme for implementing the method described above.

In another aspect of the invention there is provided a conduit sensor comprising a distributed acoustic sensor and a processor configured to take data acquired from said fibre optic distributed acoustic sensor as an object passed along the conduit; and analyse the acoustic signals detected at at least one sensing location as the object moved along the conduit so as to discriminate acoustic signals received at said sensing location from different locations.

The methods and apparatus described above use the movement of the object in the conduit, e.g. the movement of a pig in a pipeline, to discriminate between the location of various acoustic sources that may contribute signals that are detected at a given sensing portion of a DAS sensor. Additionally or alternatively the movement of the object in the conduit may also be used to detect any anomalies in the fibre deployment, for example the presence and/or extent of any fibre loops.

It will be appreciated by one skilled in the art that the DAS sensor samples the backscattered radiation from within the optical fibre at known times after the launch of the interrogating radiation to define the various sensing portions of the fibre. However the position of the sensing portions in relation to the pipeline depends on the deployment of the optical fibre. In many instances the exact deployment of the optical fibre (i.e. the fibre optic cable containing the sensing fibre) may not be exactly known but it may be assumed that optical fibre is deployed along the same path as the pipeline such a given length of fibre corresponds closely to the same length of pipeline.

In some instance however, especially when using optical fibre that was pre-installed and not originally intended for distributed acoustic sensing, the optical fibre may occasionally deviate quite significantly from such a corresponding deployment. When laying an optical fibre for communications there may be some locations where spare fibre is deployed, i.e. more of the fibre optic is deployed in a location that is needed to simply follow the path of the pipeline. For instance spare fibre may be provided to allow for splicing into the fibre if necessary. These locations where there is spare fibre are sometimes referred to as fibre loops and there may be one or more such fibre loops along the length of the pipelines.

Thus in a given section of pipeline there may be a section where the path of the optical fibre corresponds closely to the path of the pipeline, e.g. there is substantially 10 m of fibre say for each 10 m of pipeline. At the location of a fibre loop however there may be 40 m of spare fibre and thus there may be 50 m of the fibre for a given 10 m section of pipeline.

The presence of such fibre loops or other anomalies in the deployment of the fibre along the pipeline can lead to errors between the expected location of a given sensing portion and the actual position.

The method may therefore comprise monitoring the acoustic signals generated by an object as it moves through the conduit and detecting any discontinuities in the movement of said acoustic signals along the sensing portions of the fibre.

The method relies on the fact that acoustic signals generated by the movement of the object in the conduit, for example the pressure pulses produced by a pig moving in a pipeline such as described in WO2010/020796, will travel at a largely constant speed in the pipeline. Thus, if the optical fibre is deployed along a path that corresponds closely to the path of the pipeline the acoustic signals generated by the object will travel smoothly from one sensing portion to the next at a relatively constant rate. Likewise the movement of the object itself in the conduit will be reasonably regular and thus the object itself, i.e. the source of the acoustic signals, will appear to move regularly between the sensing portions.

However if a fibre loop exists the acoustic signals within the conduit will travel at a constant rate but, as the signals travel from one section of sensing fibre, past the spare fibre, and onto the next section of sensing fibre the apparent progression of the signals through the various sensing portions will experience a sudden discontinuity. The same will be true of the movement of the object itself. This discontinuity can be detected and used as an indication of an anomaly in the deployment of the fibre.

The method may also comprise using the detected acoustic signals to determine the relative spacing of the sensing portions in the location of the anomaly and/or discount, i.e. omit, any sensing portion not deployed along the length of the conduit. As mentioned above the acoustic signals generated by the movement of the object will typically travel with a locally constant velocity. Thus the signals would be expected to travel between the various sensing portions at a relatively constant rate. Thus plotting the progression of the acoustic signals through the sensing portions of the DAS sensor against time (in a waterfall plot for example) the progression of the acoustic signals would be expected to be substantially linear. In the event of a discontinuity however there may be a sudden jump where, for instance in the event of a fibre loop, the acoustic signal may apparently progress through several sensing portions near instantaneously or much faster than previously. By adjusting the relative spacing of the sensing portions in the anomalous section, or simply omitting such returns, the overall progression may be adjusted to be linear and hence the impact of the discontinuity is calibrated out.

It should be noted that this method of calibrating for inconsistent fibre deployment represents another aspect of the invention and thus, in this aspects there is provided a method of calibration of a distributed acoustic sensor deployed to monitor a conduit comprising monitoring the acoustic signals generated by an object as it moves through the conduit and detecting any discontinuities in the movement of said acoustic signals along the sensing portions of the fibre.

The invention extends to methods, apparatus and/or use substantially as herein described with reference to the accompanying drawings.

Any feature in one aspect of the invention may be applied to other aspects of the invention, in any appropriate combination. In particular, method aspects may be applied to apparatus aspects, and vice versa.

Furthermore, features implemented in hardware may generally be implemented in software, and vice versa. Any reference to software and hardware features herein should be construed accordingly.

DESCRIPTION OF THE DRAWINGS

Preferred features of the present invention will now be described, purely by way of example, with reference to the accompanying drawings, in which.

DESCRIPTION OF THE INVENTION

Figure 1:
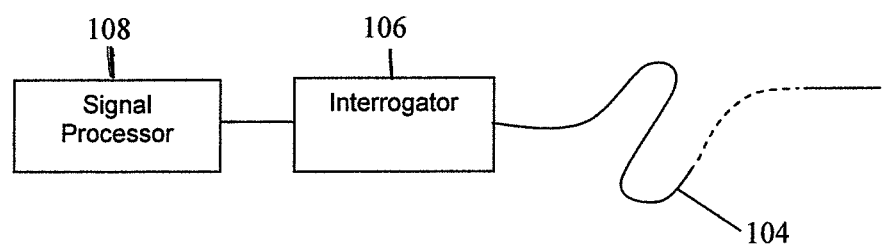
FIG. 1 illustrates the basic components of a distributed fibre optic sensor.

FIG. 1 shows a schematic of a distributed fibre optic sensing arrangement. A length of sensing fibre 104, which may be standard optic fibre such as used in telecommunication applications, is connected at one end to an interrogator 106. The output from interrogator 106 is passed to a signal processor 108 and optionally a user interface, which in practice may be realised by an appropriately specified PC. The sensing fibre can be many kilometres in length, and in this example is approximately 40 km long.

The interrogator launches an interrogating optical signal, which may for example comprise a series of pulses having a selected frequency pattern, into the sensing fibre. Backscattering results in some fraction of the light input into the fibre being reflected back to the interrogator, where it is detected to provide an output signal which is representative of acoustic disturbances in the vicinity of the fibre. The form of the optical input and the method of detection allow a single continuous fibre to be spatially resolved into discrete sensing lengths. That is, the acoustic signal sensed at one sensing length can be provided substantially independently of the sensed signal at an adjacent length. The spatial resolution in the present example is approximately 10 m, resulting in the output of the interrogator taking the form of 4000 independent data channels.

The distributed acoustic sensor may, for instance, by a distributed acoustic sensor such as described in GB patent application publication No. 2,442,745, the contents of which are hereby incorporated by reference thereto. The distributed acoustic sensor as described in GB2,442,745 is a useful sensor that employed Rayleigh backscatter but other types of distributed acoustic sensor are known and could be used instead.

In this way, the single sensing fibre can provide sensed data which is analogous to a multiplexed array of adjacent sensors, arranged in a linear path, which may be straight or curved depending on the application.

Figure 2:
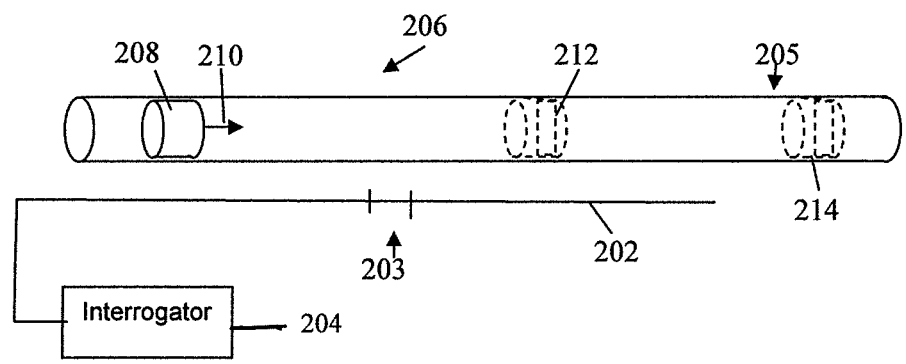
FIG. 2 shows a fibre sensor arranged along a length of pipeline.

FIG. 2 shows an arrangement employing a method according to the present invention, whereby a sensing fibre 202 (and associated interrogator and/or processor 204) is arranged along the path of a conduit, which in this example is a pipeline 206. The fibre is preferably arranged to generally follow the path of the pipeline. In this way the various discrete sensing portions of fibre correspond directly to longitudinal section of pipe. However other fibre arrangements may be used—in which case it may be necessary to know the arrangement of the fibre relative to the pipeline to allow tracking within the pipeline. The fibre may be position inside or outside of the conduit.

Distributed acoustic sensing has been demonstrated in fibre lengths of up to and beyond 40 km. Thus a single distributed acoustic sensor can provide pig tracking within 40 km of pipeline. A series of distributed acoustic sensors could be arranged to provide tracking over longer lengths of pipeline. For lengths of pipeline of the order of 80 km or so a single fibre could be used along the length of the fibre with a distributed acoustic sensor arranged at each end of the fibre. For shorter lengths of pipeline however the fibre path may double back along the pipeline to provide additional sensors for monitoring.

Referring back to FIG. 2, an acoustic source 205 may be located at a first location along the pipeline. The acoustic source 205 could, in some embodiments, be caused by a leak in pipeline and may be due to high pressure fluid escaping from the pipeline but in other embodiments could be any source of relatively constant or repetitive acoustic signals.

The location of the leak may be beyond the end of the sensing fibre 202 as shown. In conventional distributed acoustic sensing the location of the leak would not be detectable. However the acoustic signals may travel for significant distances within the pipeline—much further than the signals would travel through the ground (for a buried pipeline). Thus the noise from the leak 205 may travel along the pipeline to be sensed at a first sensing portion of the optical fibre at a location 203 of the sensing fibre (in effect the signal would be detected as noise from the end of the sensing fibre along the length of the sensing fibre until the attenuation was too great and the signal had faded to below detectable levels).

FIG. 2 also shows an object, in this instance a pig 208, located within the pipeline such that it is propelled within the pipeline in the direction 210 by the action of fluid flow within the pipeline. The pig may be inserted into the pipeline at a section of the pipeline (not shown) designed for inserting pigs.

Various types of pig are known for different purposes. For example cleaning spheres are one example of a simple pig. These comprise spheres of material designed to be propelled through the pipeline and effectively scrape the inner walls of the pipeline to remove build up of hydrocarbons on the inner walls of the pipe. Complex inspection pigs are also known. An inspection pig may be a complex data collection apparatus that is adapted to inspect the pipeline for signs or damage or degradation which may lead to failure of the pipeline.

The pig is inserted in an upstream section of pipeline and is propelled through the pipeline, generally by action of the fluid that the pipeline is carrying. Thus inspection or cleaning of the pipeline can be performed without any significant interruption to operation of the pipeline. The pig is then collected at a pig retrieval section of the pipeline (not shown) and removed.

Passage of the pig is, as mentioned, often intended to occur without interruption of the operation of the pipeline. It is therefore necessary that the pig progress through the pipeline from the insertion point to the extraction point.

The pig will have a significant effect on the acoustic signal travelling from the acoustic source 205. In effect the pig will block, or at least significantly attenuate, any signals from travelling any further along the pipeline than the pig (upstream in this example).

When the pig is first introduced upstream of the sensing portion 203 there is no effect on the acoustic signals from source 205 at that sensing location. Thus acoustic response of the sensing portion 203 will include a contribution due to the signals generated by acoustic source 205.

However when the pig travels to location 212 downstream of the relevant sensing portion 203 it will act to block the acoustic signals. Thus as the pig moves to location 212 acoustic signals due to the source 205 will cease to contribute to the response from sensing portion 203. Where the acoustic signal from the source 205 is relatively intense this may result in a step change in the detected response. Additionally or alternatively the acoustic signal from source 205 may have a characteristic, such as frequency, that suddenly stops being detected. The pig will continue to move within the pipeline and will continue to block acoustic signals from the source 205 reaching the sensing portion 203 until it has travelled further downstream of the source, e.g. to location 214. As the pig passed the location of the acoustic source 205 the acoustic signals will no longer be blocked and thus will again contribute to the response detected at sensing portion 203. Thus the signals over time as the pig moves can be used to discriminate the location of acoustic sources.

It will therefore be seen that, in the absence of a pig, a given sensing portion of fibre may receive signals directly from the local environment and also signals from any acoustic sources which are located along the pipeline and which are transmitted via the pipeline itself. When a pig is introduced into the pipeline and traverses at least part of the pipeline it effectively blocks, or at least attenuates, the signals from the opposite side of the pig from reaching a given sensing portion. As the pig moves it therefore effectively scans the various possible locations for acoustic sources across a given sensing portion. In such a case a pre-existing signal will thus be detected at a given sensing portion. The signal will then disappear as the pig comes between the source and the sensing portion. This may happen relatively quickly. The particular signal may then remain undetected for a period as the pig traverses the distance between the source and the sensing portion but once the pig is no longer between the source and the sensing portion the signal will re-appear—again possibly relatively quickly.

This characteristic of a pre-existing signal disappearing and then re-appearing in the response of a given sensing portion can thus be used as a characteristic to detect a signal which is due to transmission of acoustic signals along the pipeline—assuming the pig does actually pass by the location of the relevant sensing portion. In such a case the correlation of the disappearance and/or re-appearance of the signal with the position of the pig passing the location of the relevant sensing portion may also be used to detect that a given signal is/was being blocked by the pig. Thus looking for a characteristic signal that appears/disappears as the pig passes the sensing portion can be used to identify a signal due to a remote source. In this case the position of the pig at the time that the signal disappeared/re-appeared can then be used to determine the location of the source along the pipeline and this, as mentioned, applies even if the location is outside the section of the pipeline that is monitored by the DAS sensor. This does of course require the position of the pig to be known but this could be determined by a location tracking module on the pig itself and/or by extrapolating the position of the pig based on the detected motion when it passed through the monitored section of pipeline.

It will be appreciated however that it is not necessary for the pig to actually pass through the monitored section of pipeline, i.e. that monitored by the sensing fibre. All that is required is for the pig to move from being located between the relevant source and sensing location in the pipeline to not being located between the source and sensing portion (or vice versa).

The discussion above has focussed on looking at the returns from a single sensing portion of fibre but in practice the returns from a plurality of different sensing portions may be analysed in the same way and the various signals that are detected or cease to be detected as the pig moves past the relevant sensing location may be analysed and/or correlated to aid in detecting those signals which are due to remote sources.

Also frequency analysis and/or other correlation techniques may be applied to identify a given signal that occurs, ceases and then re-occurs.

Figure 3:
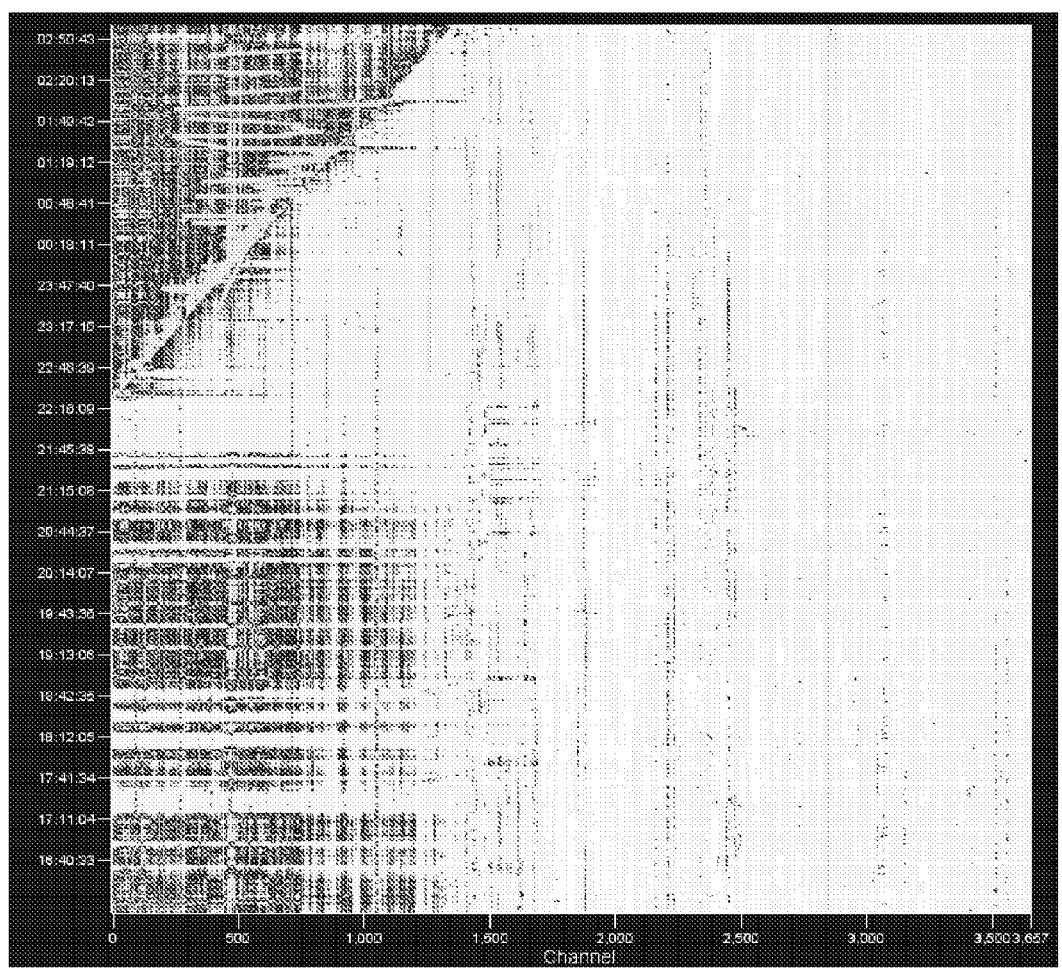
FIG. 3 illustrates data obtained from a pipeline.

FIG. 3 shows actual data from a fibre optic sensor along the length of a pipeline during a pigging run. The data is shown as a waterfall type plot with distance along the fibre from the end along the x-axis and time along the y-axis with intensity represented by brightness.

It can be seen that in the bottom left hand corner of the plot there is some noise. This represents a noise source off the end of the fibre which affects all the sensing channels at the end of the fibre. At a time 21:45 the noise is cut off at the pig passes the noise source. The noise remains cut off until the pig then travels along the channels (the diagonal line along the top left). By looking at the slop of the diagonal line the speed of the pig can be determine which can extrapolated backwards to the time at which the noise was cut off to determine the location of the acoustic source.

The discussion above has assumed that the optical fibre is deployed along the same path as the pipeline such that the position of a sensing portion along the length of the fibre corresponds to the same position along the length of the pipeline (or the mapping of the sensing portions of the fibre to the position along the pipeline is otherwise know).

Figure 4A:
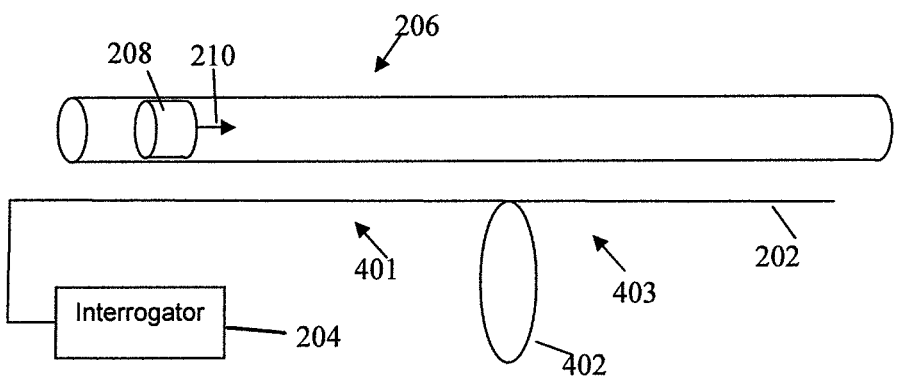
FIGS. 4a and 4b illustrate a fibre deployment including a fibre loop and the resulting waterfall plot.

In some instances however, especially where a pre-existing fibre is used for distributed acoustic sensing, the exact deployment of the fibre to the path of the pipeline may not be known. For instance the fibre may be deployed largely along the path of the pipeline but there may be one or more sections of fibre loops where spare fibre was located, either inadvertently during deployed or deliberately to provide ease of access or to allow for later re-routing. FIG. 4a illustrates a pipeline 206 with a sensing fibre 202 used with a DAS interrogator 204 to provide a DAS sensor.

In this example a first section 401 of fibre 202 is deployed substantially along the path of the pipeline. However a second section 402 comprises a fibre loop and thus there is a relatively large length of fibre by a small section of pipeline. In a third section 403 the fibre is again deployed along the path of the pipeline.

In this embodiment the length into the fibre in the first section corresponds well to the length along the pipeline (allowing for the length of fibre that connects to the interrogator 204). However for section 403 the location of the sensing portions relative to the pipeline depends on the length of fibre loop 402. If the existence, location and length of loop 402 are uncertain this can lead to a considerable uncertainty in which parts of the pipeline are being monitored in section 403.

In embodiments of the present invention however the acoustic signals generated by motion of a pig 208 in the pipeline are used to detect any anomalies in the fibre deployment. As the pig moves it will generate acoustic signals, for instance pressure pulses as it passes the weld joints of the pipeline. These acoustic signals will propagate along the pipeline for a significant distance and may be detected by the sensing portions of fibre.

Figure 4B:
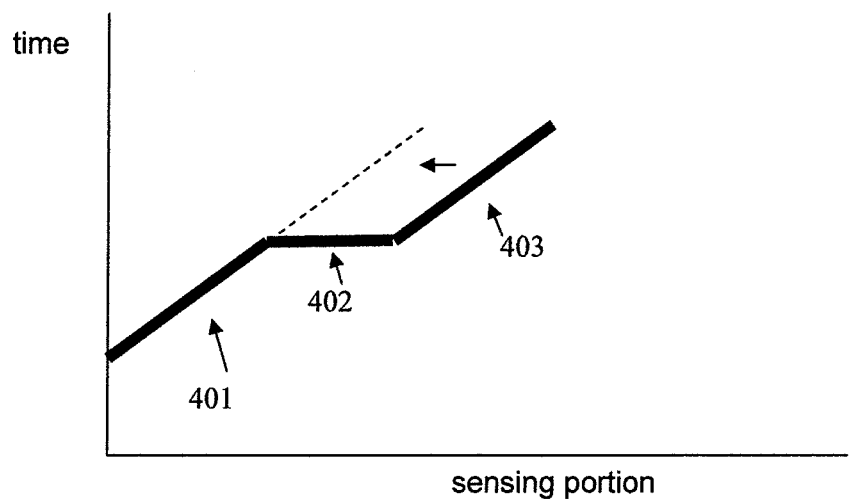

FIG. 4b illustrates how an acoustic signal may be detected and shows again a waterfall type plot of time against sensing portion. As the acoustic signal will travel at a substantially constant speed then in a section where the sensing portions correspond to the path of the pipeline then the acoustic signal will move regularly between the sensing portions so as to produce a linear plot—where the gradient depends on the propagation speed. At the fibre loop however the signal will appear to travel very quickly past several sensing portions before, at section 403, resuming the same linear progress as previously.

It can therefore be seen that by monitoring the acoustic signals generated by the movement of the pig any discontinuities in the fibre deployment can be detected. Further by looking at the gradient before and after the discontinuity the sensing portions in the area of discontinuity can be adjusted (in terms of spacing) or omitted so that the overall characteristic maintains a regular propagation. Thus as shown in FIG. 4b the sensing portions corresponding to the fibre loop 402 can be omitted to effectively calibrate the locations of the later sensing portions, as indicated by the arrow and dotted line corresponding to the calibrated response.

Each feature disclosed in the description, and (where appropriate) the claims and drawings may be provided independently or in any appropriate combination.

The invention claimed is:

1. A method of conduit monitoring comprising:
    taking data acquired from at least part of a conduit using a fibre optic distributed acoustic sensor as an object passed along the conduit, said data corresponding to acoustic signals detected at each of a plurality of sensing locations of the fibre optic distributed acoustic sensor; and
    analysing the acoustic signals detected at at least one sensing location as the object moves along the conduit to determine whether the presence of the object attenuates an acoustic signal so as to discriminate acoustic signals received at said sensing location from different locations.

2. A method as claimed in claim 1 wherein the conduit is a pipeline.

3. A method as claimed in claim 2 wherein the object is a pipeline pig.

4. A method as claimed in claim 1 wherein the step of analysing the acoustic signals comprises locating the position along the conduit of an acoustic source.

5. A method as claimed in claim 1 wherein the step of analysing the acoustic signals comprises determining at what point in time a particular acoustic signal is detected or not detected at a sensing location.

6. A method as claimed in claim 5 comprising, identifying a first acoustic signal and identifying when the first acoustic signal starts to be detected and/or ceases to be detected.

7. A method as claimed in claim 6 comprising identifying when the first signal both ceases to be detected and also when the first signal re-starts to be detected.

8. A method as claimed in claim 5 comprising determining the location of the object at the point in time that a particular acoustic signal is detected or not detected.

9. A method as claimed in claim 8 wherein the location of the object is determined by (i) a location tracking device on the object or (ii) monitoring the acoustic signals created by the object as it moves down the conduit.

10. A method as claimed in claim 1 comprising identifying the location of a leak in a pipeline by: identifying acoustic signals associated with a leak, and identifying when the acoustic signals associated with the leak cease to be detected and/or start to be detected as a pig travels in the pipeline.

11. A method as claimed in claim 1 comprising applying differential analysis to acoustic signals from a given sensing location acquired with the object at one location and acoustic signals acquired from said sensing location acquired with the object at at least one other location and/or without the object in the conduit.

12. A method as claimed in claim 1 wherein the said data is data acquired by said fibre optic distributed acoustic sensor as at least two objects move within the conduit.

13. A method as claimed in claim 1 comprising analysing the acoustic signals produced by the movement of the object in the conduit to detect any anomalies in the deployment of an optical fibre of the fibre optic distributed acoustic sensor.

14. A computer programme which, when run on a suitable computer, performs the method of claim 1.

15. A method as claimed in claim 1 wherein the step of analysing the acoustic signals comprising identifying a first acoustic signal, determining a time at which the object starts to attenuate the first acoustic signal and a time at which the object ceases to attenuate the first acoustic signal, and determining a location of a source of the first acoustic signal by considering the location of the object at those times.

16. A method as claimed in claim 15 comprising identifying the location of an acoustic source along the conduit in a section of the conduit which is not monitored using the fibre optic distributed acoustic sensor.

17. A method as claimed in claim 1 which comprises monitoring at least part of a conduit using a fibre optic distributed acoustic sensor as an object passes along the conduit.

18. A method of extending the range or sensing capability of a conduit monitoring sensor comprising a fibre optic distributed acoustic sensor having a fibre optic cable deployed along a first section of the conduit, the method comprising analysing acoustic signals detected by the fibre optic distributed acoustic sensor at at least one sensing portion of interest in a period when an object is travelling through a second, different section of the conduit so as to identify the location of an acoustic source along the conduit in the second section of the conduit.

19. A method as claimed in claim 18 comprising analyzing the acoustic signals detected during the period that the object moves through the conduit and detecting any discontinuities in the movement of said acoustic signals along the sensing portions of the fibre.

20. A method as claimed in claim 18 comprising using the acoustic signals detected to determine the relative spacing of the sensing portions in the location of the anomaly and/or discount any sensing portion not deployed along the length of the conduit.

21. A conduit sensor comprising:

a fibre optic distributed acoustic sensor; and a processor configured to take data acquired from said fibre optic distributed acoustic sensor as an object passed along the conduit, said data comprising acoustic signals detected at each of a plurality of sensing locations; and analyse the acoustic signals detected at at least one sensing location as the object moved along the conduit to determine whether the presence of the object attenuates an acoustic signal so as to discriminate acoustic signals received at said sensing location from different locations.

* * * * *